US006528536B1

(12) United States Patent
Schelberger et al.

(10) Patent No.: US 6,528,536 B1
(45) Date of Patent: Mar. 4, 2003

(54) FUNGICIDAL MIXTURES

(75) Inventors: Klaus Schelberger, Gönnheim; Maria Scherer, Landau; Hubert Sauter, Mannheim; Bernd Müller, Frankenthal; Erich Birner, Altleiningen; Joachim Leyendecker, Ladenburg; Eberhard Ammermann, Heppenheim; Gisela Lorenz, Neustadt; Siegfried Strathmann, Limburgerhof; Reinhold Saur, Böhl-Iggelheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/423,882

(22) PCT Filed: May 13, 1998

(86) PCT No.: PCT/EP98/02820

§ 371 (c)(1),
(2), (4) Date: Nov. 15, 1999

(87) PCT Pub. No.: WO98/52417

PCT Pub. Date: Nov. 26, 1998

(30) Foreign Application Priority Data

May 22, 1997 (DE) .......................................... 197 21 401
May 22, 1997 (DE) .......................................... 197 21 402

(51) Int. Cl.$^7$ ........................ A01N 43/56; A01N 43/64; A01N 37/06; A01N 37/18; A01N 37/12
(52) U.S. Cl. ........................ 514/407; 514/384; 514/539; 514/549; 514/619
(58) Field of Search ................ 514/407, 384, 514/549, 539, 619

(56) References Cited

U.S. PATENT DOCUMENTS 4,829,085 A    5/1989    Wenderoth et al. ......... 514/522

FOREIGN PATENT DOCUMENTS

EP          254 426        1/1988

(List continued on next page.)

OTHER PUBLICATIONS

Tomlin, The Pesticide Manual Incorporating the Agrochemicals Handbook, 10$^{th}$ ed. (1995) pp. 359–1360.*

Primary Examiner—Allen J. Robinson
(74) Attorney, Agent, or Firm—Keil & Weinkauf

(57) ABSTRACT

A fungicidal mixture comprises
a$_1$) a phenyl benzyl ether derivative of the formula I.a, I.b or I.c

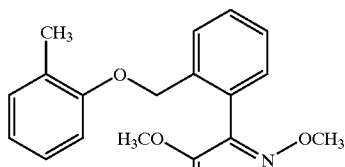
I.a

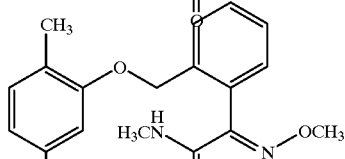
I.b

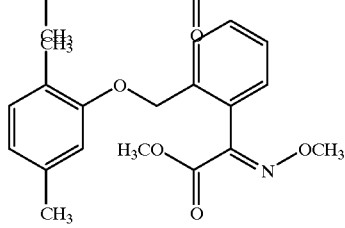
I.c and/or
a$_2$) a carbamate of the formula Id

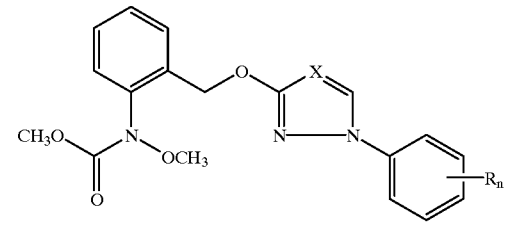
(I)

where X is CH or N, n is 0, 1 or 2 and R is halogen, $C_1$–$C_4$-alkyl or $C_1$–$C_4$-haloalkyl, it being possible for the radicals R to be different if n is 2, or one of its salts or adducts, and b) a dinitrophenol derivative of the formula II.a or II.b

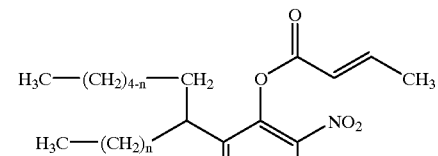
II.a

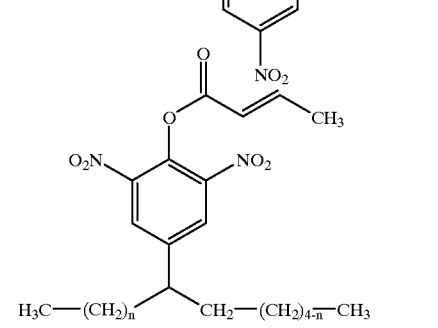
II.b where n is 0, 1 or 2
in a synergistically effective amount.

19 Claims, No Drawings

FOREIGN PATENT DOCUMENTS

| | | | |
|---|---|---|---|
| EP | 0398692 | * | 11/1990 |
| WO | 9601256 | * | 1/1996 |
| WO | 9601258 | * | 1/1996 |

* cited by examiner

FUNGICIDAL MIXTURES

This application is a 371 of PCT/EP 98/02820, filed May 13, 1998.

The present invention relates to a fungicidal mixture which comprises $a_1$) a phenyl benzyl ether derivative of the formula I.a, I.b or I.c

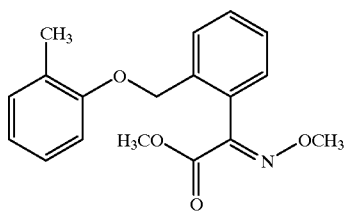

I.a

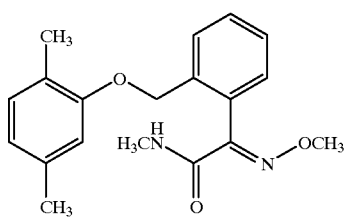

I.b

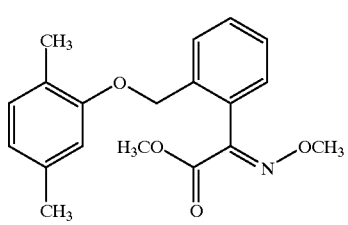

I.c and/or $a_2$) a carbamate of the formula Id

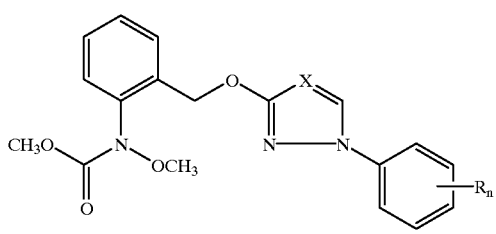

(I)

where X is CH or N, n is 0, 1 or 2 and R is halogen, $C_1$–$C_4$-alkyl or $C_1$–$C_4$-haloalkyl, it being possible for the radicals R to be different if n is 2, or one of its salts or adducts, and b) a dinitrophenol derivative of the formula II.a or II.b

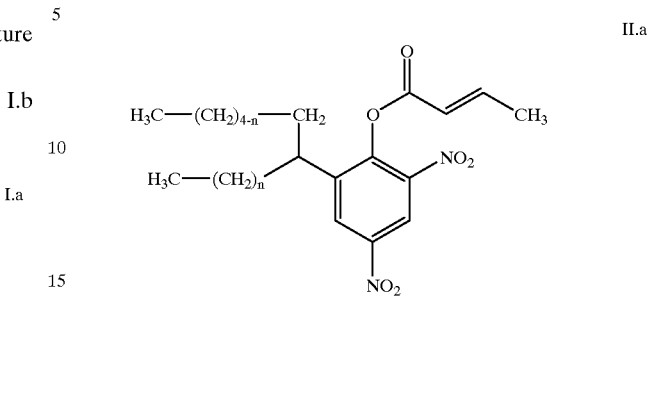

where n is 0, 1 or 2 in a synergistically effective amount.

The invention further relates to methods for controlling harmful fungi using mixtures of the compounds I (I.a, I.b or I.c) and II (II.a or II.b) and to the use of the compound I and the compound II for preparing such mixtures.

The compounds of the formula Ia-c, their preparation and their activity against harmful fungi are known from the literature (EP-A 253 213; EP-A 254 426; EP-A 398 692).

The compounds of the formula Id, their preparation and their activity are known from WO-A 93/15046, WO-A 96/01256 and WO-A 96/01258.

Also known is the mixture of the compounds II (II.a and II.b) (common name: Dinocap), their preparation and their activity against harmful fungi and arachnids (U.S. Pat. Nos. 2,526,660; 2,810,767).

It is an object of the present invention to provide mixtures which have an improved activity against harmful fungi combined with a reduced total amount of active ingredients applied (synergistic mixtures), with a view to reducing the application rates and to improving the activity spectrum of the known compounds I and II.

We have found that this object is achieved by the mixture defined at the outset. In addition, we have found that, by applying the compound I and the compound II simultaneously, that is to say separately as well as together, or by applying the compound I and the compounds II in succession, better control of harmful fungi is possible than when the individual compounds are used.

The formula Id in particular represents carbamates where the combination of the substituents corresponds to a row of the table below:

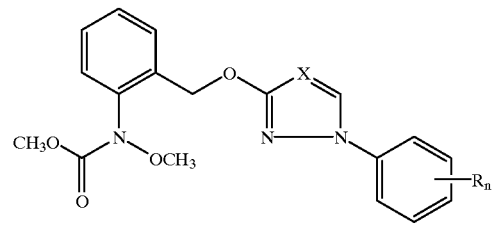

(I)

| No. | X | $R_n$ |
|---|---|---|
| I.1 | N | 2-F |
| I.2 | N | 3-F |
| I.3 | N | 4-F |
| I.4 | N | 2-Cl |
| I.5 | N | 3-Cl |
| I.6 | N | 4-Cl |
| I.7 | N | 2-Br |
| I.8 | N | 3-Br |
| I.9 | N | 4-Br |
| I.10 | N | 2-CH$_3$ |
| I.11 | N | 3-CH$_3$ |
| I.12 | N | 4-CH$_3$ |
| I.13 | N | 2-CH$_2$CH$_3$ |
| I.14 | N | 3-CH$_2$CH$_3$ |
| I.15 | N | 4-CH$_2$CH$_3$ |
| I.16 | N | 2-CH(CH$_3$)$_2$ |
| I.17 | N | 3-CH(CH$_3$)$_2$ |
| I.18 | N | 4-CH(CH$_3$)$_2$ |
| I.19 | N | 2-CF$_3$ |
| I.20 | N | 3-CF$_3$ |
| I.21 | N | 4-CF$_3$ |
| I.22 | N | 2,4-F$_2$ |
| I.23 | N | 2,4-Cl$_2$ |
| I.24 | N | 3,4-Cl$_2$ |
| I.25 | N | 2-Cl, 4-CH$_3$ |
| I.26 | N | 3-Cl, 4-CH$_3$ |
| I.27 | CH | 2-F |
| I.28 | CH | 3-F |
| I.29 | CH | 4-F |
| I.30 | CH | 2-Cl |
| I.31 | CH | 3-Cl |
| I.32 | CH | 4-Cl |
| I.33 | CH | 2-Br |
| I.34 | CH | 3-Br |
| I.35 | CH | 4-Br |
| I.36 | CH | 2-CH$_3$ |
| I.37 | CH | 3-CH$_3$ |
| I.38 | CH | 4-CH$_3$ |
| I.39 | CH | 2-CH$_2$CH$_3$ |
| I.40 | CH | 3-CH$_2$CH$_3$ |
| I.41 | CH | 4-CH$_2$CH$_3$ |
| I.42 | CH | 2-CH(CH$_3$)$_2$ |
| I.43 | CH | 3-CH(CH$_3$)$_2$ |
| I.44 | CH | 4-CH(CH$_3$)$_2$ |
| I.45 | CH | 2-CF$_3$ |
| I.46 | CH | 3-CF$_3$ |
| I.47 | CH | 4-CF$_3$ |
| I.48 | CH | 2,4-F$_2$ |
| I.49 | CH | 2,4-Cl$_2$ |
| I.50 | CH | 3,4-Cl$_2$ |
| I.51 | CH | 2-Cl, 4-CH$_3$ |
| I.52 | CH | 3-Cl, 4-CH$_3$ |

Particular preference is given to the compounds I.12, I.23, I.32 and I.38.

When preparing the mixtures, it is preferred to employ the pure active ingredients I and II, to which further active ingredients against harmful fungi or other pests, such as insects, arachnids or nematodes, or else herbicidal or growth-regulating active ingredients or fertilizers can be admixed.

The mixtures of the compounds I and II, or the simultaneous joint or separate use of the compounds I and II, have outstanding action against a wide range of phytopathogenic fungi, in particular from the classes of the Ascomycetes, Basidiomycetes, Phycomycetes and Deuteromycetes. Some of them act systemically and can therefore also be employed as foliar and soil-acting fungicides.

They are especially important for controlling a large number of fungi in a variety of crop plants, such as cotton, vegetable species (eg. cucumbers, beans, tomatoes, potatoes and cucurbits), barley, grass, oats, bananas, coffee, maize, fruit species, rice, rye, soya, grapevine, wheat, ornamentals, sugar cane, and a variety of seeds.

They are particularly suitable for controlling the following phytopathogenic fungi: *Erysiphe graminis* (powdery mildew) in cereals, *Erysiphe cichoracearum* and *Sphaerotheca fuliginea* in cucurbits, *Podosphaera leucotricha* in apples, *Uncinula necator* in grapevines, Puccinia species in cereals, Rhizoctonia species in cotton, rice and lawns, Ustilago species in cereals and sugar cane, *Venturia inaequalis* (scab) in apples, Helminthosporium species in cereals, *Septoria nodorum* in wheat, *Botrytis cinerea* (gray mold) in strawberries, vegetables, ornamentals and grapevines, *Cercospora arachidicola* in groundnuts, *Pseudocercosporella herpotrichoides* in wheat and barley, *Pyricularia oryzae* in rice, *Phytophthora infestans* in potatoes and tomatoes, *Plasmopara viticola* in grapevines Pseudocercosporella species in hops and cucumbers, Alternaria species in vegetables and fruit, Mycosphaerella species in bananas, and Fusarium and Verticillium species.

Furthermore, they can be used in the protection of materials (eg. in the protection of wood), for example against *Paecilomyces variotii*.

The compounds I and II can be applied simultaneously, that is either together or separately, or in succession, the sequence, in the case of separate application, generally not having any effect on the result of the control measures.

The compounds I and II are usually in a weight ratio of 10:1 to 0.01:1, preferably 5:1 to 0.05:1, in particular 1:1 to 0.05:1.

Depending on the nature of the desired effect, the application rates of the mixtures according to the invention are, in particular, in agricultural crops, from 0.01 to 8 kg/ha, preferably 0.1 to 5 kg/ha, in particular 0.5 to 3.0 kg/ha.

The application rates are, in the case of the compounds I, from 0.01 to 2.5 kg/ha, preferably 0.05 to 2.5 kg/ha, in particular 0.05 to 1.0 kg/ha.

In the case of the compounds II, the application rates are from 0.01 to 10 kg/ha, preferably 0.05 to 5 kg/ha, in particular 0.1 to 2.0 kg/ha.

For seed treatment, the application rates of the mixture are generally from 0.001 to 250 g/kg of seed, preferably 0.01 to 100 g/kg, in particular 0.01 to 50 g/kg.

If phytopathogenic harmful fungi are to be controlled, the separate or joint application of the compounds I and II or of the mixtures of the compounds I and II is effected by spraying or dusting the seeds, the plants or the soils before or after sowing of the plants, or before or after plant emergence.

The fungicidal synergistic mixtures according to the invention, or the compounds I and II, can be formulated for example in the form of ready-to-spray solutions, powders and suspensions or in the form of highly concentrated aqueous, oily or other suspensions, dispersions, emulsions, oil dispersions, pastes, dusts, materials for spreading or granules, and applied by spraying, atomizing, dusting, spreading or pouring. The use form depends on the intended purpose; in any case, it should guarantee as fine and uniform as possible a distribution of the mixture according to the invention.

The formulations are prepared in a manner known per se, eg. by adding solvents and/or carriers. It is usual to admix inert additives, such as emulsifiers or dispersants, to the formulations.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene; or polyoxypropylene alkyl ethers lauryl alcohol polyglycol ether acetate, sorbitol esters, lignosulfite waste liquors or methylcellulose.

Powders, materials for spreading and dusts can be prepared by mixing or jointly grinding the compounds I and II or the mixture of the compounds I and II with a solid carrier.

Granules (eg. coated granules, impregnated granules or homogeneous granules) are usually prepared by binding the active ingredient, or active ingredients, to a solid carrier.

Fillers or solid carriers are, for example, mineral earths, such as silica gel, silicic acids, silica gels, silicates, talc, kaolin, limestone, lime, chalk, bole, loess, clay, dolomite, diatomaceous earth, calcium sulfate, magnesium sulfate, magnesium oxide, ground synthetic materials, and fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise 0.1 to 95% by weight, preferably 0.5 to 90% by weight, of one of the compounds I or II or of the mixture of the compounds I and II. The active ingredients are employed in a purity of from 90% to 100%, preferably 95% to 100% (according to NMR spectrum or HPLC.

The compounds I and II, or the mixtures, or the corresponding formulations, are applied by treating the harmful fungi, their habitat, or the plants, seeds, soils, areas, materials or spaces to be kept free from them with a fungicidally effective amount of the mixture, or of the compounds I and II in the case of separate application.

Application can be effected before or after infection by the harmful fungi.

Use Example

The synergistic action of the mixtures according to the invention was demonstrated by the following experiments:

The active ingredients, separately or together, were formulated as a 10% emulsion in a mixture of 70% by weight of cyclohexanone, 20% by weight of Nekanil® LN (Lutensol® AP6, wetting agent having emulsifying and dispersing action, based on ethoxylated alkylphenols) and 10% by weight of Emulphor® EL (Emulan® EL, emulsifier based on ethoxylated fatty alcohols) and diluted with water to give the desired concentration.

EXAMPLE 1

Activity against powdery mildew of wheat

Leaves of wheat seedlings cv. "Frü hgold" which had been grown in pots were sprayed to runoff point with an aqueous preparation of active ingredient which had been made from a stock solution comprising 10% of active compound, 63% of cyclohexanone and 27% of emulsifier, and, 24 hours after the spray coating had dried on, were dusted with spores of powdery mildew of wheat (Erysiphe graminis forma specialis tritici). The test plants were subsequently placed in a greenhouse at from 20 to 24° C. and a relative atmospheric humidity of 70 to 90%. After 7 days, the extent of mildew development was determined visually in % infection of the total leaf area.

Evaluation was carried out by determining the infected leaf areas in percent. These percentages were converted into degrees of action. The efficacy (E) was calculated as follows using Abbot's formula:

$$E = (1-\alpha) \cdot 100/\beta$$

α corresponds to the fungal infection of the treated plants in % and

β corresponds to the fungal infection the untreated (control) plants in %

A degree of action of 0 means that the infection level of the treated plants corresponds to that of the untreated control plants; a degree of action of 100 means that the treated plants were not infected.

The expected degrees of action of the mixtures of the active ingredients were determined using Colby's formula [R. S. Colby, Weeds 15, (1967) 20–22] and compared with the observed degrees of action.

$$\text{Colby's formula:} E = x+y-x \cdot y/100$$

E expected degree of action, expressed in % of the untreated control, when using the mixture of the active ingredients A and B at the concentrations a and b x degree of action, expressed in % of the untreated control, when using active ingredient A at a concentration of a y degree of action, expressed in % of the untreated control, when using active ingredient B at a concentration of b The results of the activity against powdery mildew of wheat are shown in the tables that follow.

| Ex. | Active ingredient | Concentration of active ingredient in the spray liquor in ppm | Efficacy in % of the untreated contol |
|---|---|---|---|
| 1V | Control (untreated) | (100% infestation) | 0 |
| 2V | Ia | 0.6 | 0 |
|  |  | 0.3 | 0 |
| 3V | Ib | 0.6 | 15 |
|  |  | 0.3 | 15 |
| 4V | Compound I.32 (Id) | 0.63 | 75 |
|  |  | 0.31 | 40 |
| 5V | IIa | 12.5 | 10 |
|  |  | 6.3 | 0 |
|  |  | 3.1 | 0 |

TABLE 3

| Ex. | Mixture according to the invention | Observed efficacy | Calculated efficacy*) |
|---|---|---|---|
| 6 | 0.6 ppm Ia + 12.5 ppm IIa | 40 | 10 |
| 7 | 0.3 ppm Ia + 12.5 ppm IIa | 40 | 10 |
| 8 | 0.6 ppm Ib + 12.5 ppm IIa | 85 | 23.5 |

TABLE 3-continued

| Ex. | Mixture according to the invention | Observed efficacy | Calculated efficacy*) |
|---|---|---|---|
| 9 | 0.3 ppm Ib<br>+<br>12.5 ppm IIa | 80 | 23.5 |
| 10 | 0.63 ppm Id<br>+<br>6.3 ppm IIa | 95 | 75 |
| 11 | 0.31 ppm Id<br>+<br>3.1 ppm IIa | 80 | 40 |

*)calculated using Colby's formula

The test results show that the observed efficacy in all mixing ratios is higher than the efficacy that had been calculated beforehand using Colby's formula.

We claim:

1. A fungicidal composition comprising synergistically effective amounts of a₂) a carbamate of formula Id

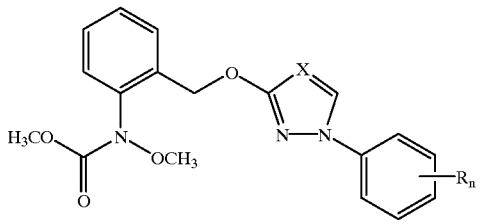

(Id)

wherein X is CH or N, n is 0, 1 or 2, and R is halogen, $C_1$–$C_4$-alkyl or $C_1$–$C_4$-haloalkyl, wherein the radicals R are identical or differenct when n is 2, or one of its salts or adducts, and b) a dinitrophenol II which is a compound of formula II.a or formula II.b

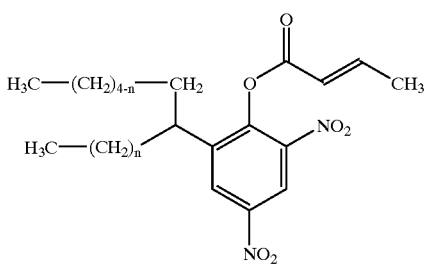

II.a

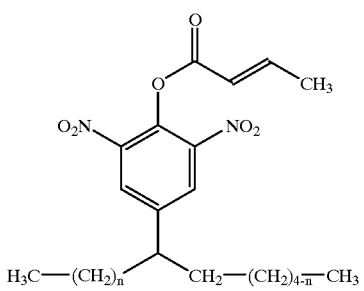

II.b wherein n is 0, 1 or 2, or is a combination of the compounds of formulae II.a and II.b, and comprising the carbamate of formula Id and the dinitrophenol II in a weight ratio of from 10:1 to 0.01:1.

2. The composition defined in claim 1 which is conditioned in two parts, one part comprising the carbamate of formula Id in a solid or liquid carrier, and the other part comprising the dinitrophenol II in a solid or liquid carrier.

3. The composition defined in claim 1, wherein X is CH and R is halogen.

4. The composition defined in claim 1, further comprising a synergistically effective amount of a phenyl benzyl ether I of the formula

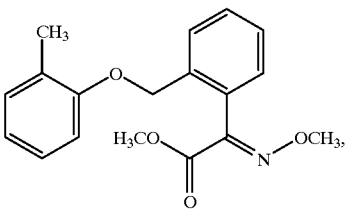

I.a

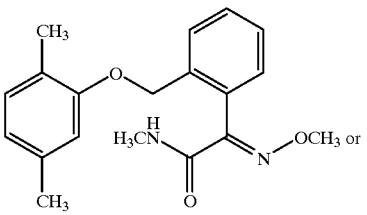

I.b

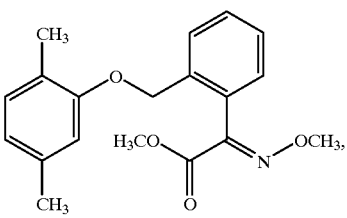

I.c and comprising (i) the carbamate of formula Id and the phenyl benzyl ether I and (ii) the dinitrophenol II in a weight ratio of from 10:1 to 0.01:1.

5. The composition defined in claim 4 which is conditioned in two parts, one part comprising the carbamate of formula Id and the phenyl benzyl ether I in a solid or liquid carrier, and the other part comprising the dinitrophenol II in a solid or liquid carrier.

6. The composition defined in claim 4, wherein X is CH and R is halogen.

7. The composition defined in claim 1 wherein the dinitrophenol II is the combination of the compounds of formulae II.a and II.b.

8. A method for controlling harmful fungi, which comprises treating the harmful fungi, their habitat, or plants, seeds, soils, areas, materials or spaces to be kept free from said fungi with synergistically effective amounts of the carbamate of formula Id and the dinitrophenol II as set forth in claim 1, wherein the carbamate of formula Id and the dinitrophenol II are applied in a weight ratio of from 10:1 to 0.01:1.

9. The method of claim 8, wherein the carbamate of formula Id and the dinitrophenol II are applied simultaneously, that is to say separately as well as together, or in succession.

10. The method of claim 8, wherein the carbamate of formula Id is applied in an amount of from 0.01 to 2.5 kg/ha.

11. The method of claim 8, wherein the dinitrophenol II is applied in an amount of from 0.01 to 10 kg/ha.

12. The method of claim 8, wherein x is CH and R is halogen.

13. The method of claim 8, wherein the dinitrophenol II is a combination of the compounds of formulae II.a and II.b.

14. A method for controlling harmful fungi, which comprises treating the harmful fungi, their habitat, or plants, seeds, soils, areas, materials or spaces to be kept free from said fungi with synergistically effective amounts of the carbamate of formula Id, the phenyl benzyl ether I and the dinitrophenol II set forth in claim 4, wherein (i) the carbamate of formula Id and the phenyl benzyl ether I and (ii) the dinitrophenol II are applied in a weight ratio of from 10:1 to 0.01:1.

15. The method of claim 14, wherein the carbamate of formula Id, the phenyl benzyl ether I and the dinitrophenol II are applied simultaneously separately as well as together, or in succession.

16. The method of claim 14, wherein the carbamate of formula Id is applied in an amount of from 0.01 to 2.5 kg/ha.

17. The method of claim 14, wherein the phenyl benzyl ether I is applied in an amount of from 0.01 to 2.5 kg/ha.

18. The method of claim 14, wherein the dinitrophenol II is applied in an amount of from 0.01 to 10 kg/ha.

19. The method of claim 14, wherein x is CH and R is halogen.

* * * * *

UNITED STATES PATENT AND TRADEMARK OFFICE
CERTIFICATE OF CORRECTION

PATENT NO.   : 6,528,536 B1
DATED        : March 4, 2003
INVENTOR(S)  : Schelberger et al.

It is certified that error appears in the above-identified patent and that said Letters Patent is hereby corrected as shown below:

Title page,
Item [57], ABSTRACT, formulae I.a, I.b and I.c should be spaced out properly as follows:

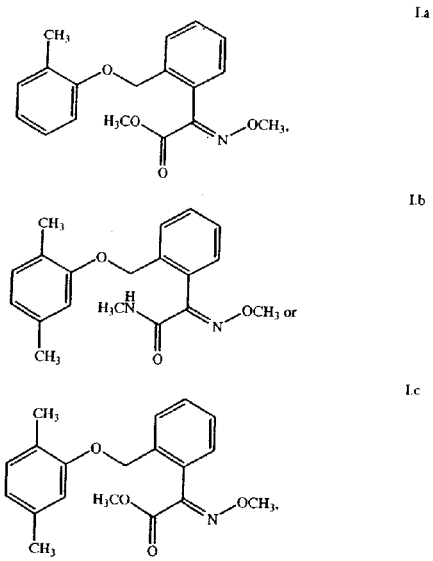

Column 7,
Line 37, "differenct" should be -- different --.

Signed and Sealed this

Twenty-fourth Day of June, 2003

JAMES E. ROGAN
*Director of the United States Patent and Trademark Office*